United States Patent [19]

Olin

[11] Patent Number: 4,863,459
[45] Date of Patent: Sep. 5, 1989

[54] BI-LEAFLET HEART VALVE

[76] Inventor: Christian L. Olin, Weibulls v. 2, S-223 65 Lund, Sweden

[21] Appl. No.: 141,209

[22] Filed: Jan. 6, 1988

[51] Int. Cl.$^4$ ............................................... A61F 2/24
[52] U.S. Cl. ......................................................... 623/2
[58] Field of Search ............................................. 623/2

[56] References Cited

U.S. PATENT DOCUMENTS

| | | |
|---|---|---|
| 3,749,359 | 7/1973 | Montesi . |
| 3,903,548 | 9/1975 | Nakib . |
| 4,011,601 | 3/1977 | Clune et al. . |
| 4,306,319 | 12/1981 | Kaster . |
| 4,328,592 | 5/1982 | Klawitter ............................... 623/2 |
| 4,373,216 | 2/1983 | Klawitter . |
| 4,484,365 | 11/1984 | Murquet et al. . |
| 4,605,408 | 8/1986 | Carpentier . |
| 4,676,789 | 6/1987 | Sorensen ............................... 623/2 |

FOREIGN PATENT DOCUMENTS 0211576 2/1987 European Pat. Off. ............... 623/2

Primary Examiner—Richard J. Apley
Assistant Examiner—James Prizant
Attorney, Agent, or Firm—Fitch, Even, Tabin & Flannery

[57] ABSTRACT

Disclosed is a heart valve prosthesis having an annular valve body defining a central passageway for blood flow. A pair of curved, convex-concave leaflet occluders pivotally mounted in the valve body and movable between open and closed positions have opposed lateral edges disposed between a mating edge and an arcuate edge. The mating edges of the leaflets engage each other when the valve is closed, with the arcuate edges engaging a preferably frustoconical section of the valve body. A pair of protuberances extend from the valve body to pivotally mount each lateral edge of each leaflet. Each pair of protuberances receives a lateral edge of a leaflet therebetween. The leaflets include a swelled area having a concave lower surface for receiving one protuberance and an upper convex surface for engaging the other protuberance.

6 Claims, 2 Drawing Sheets

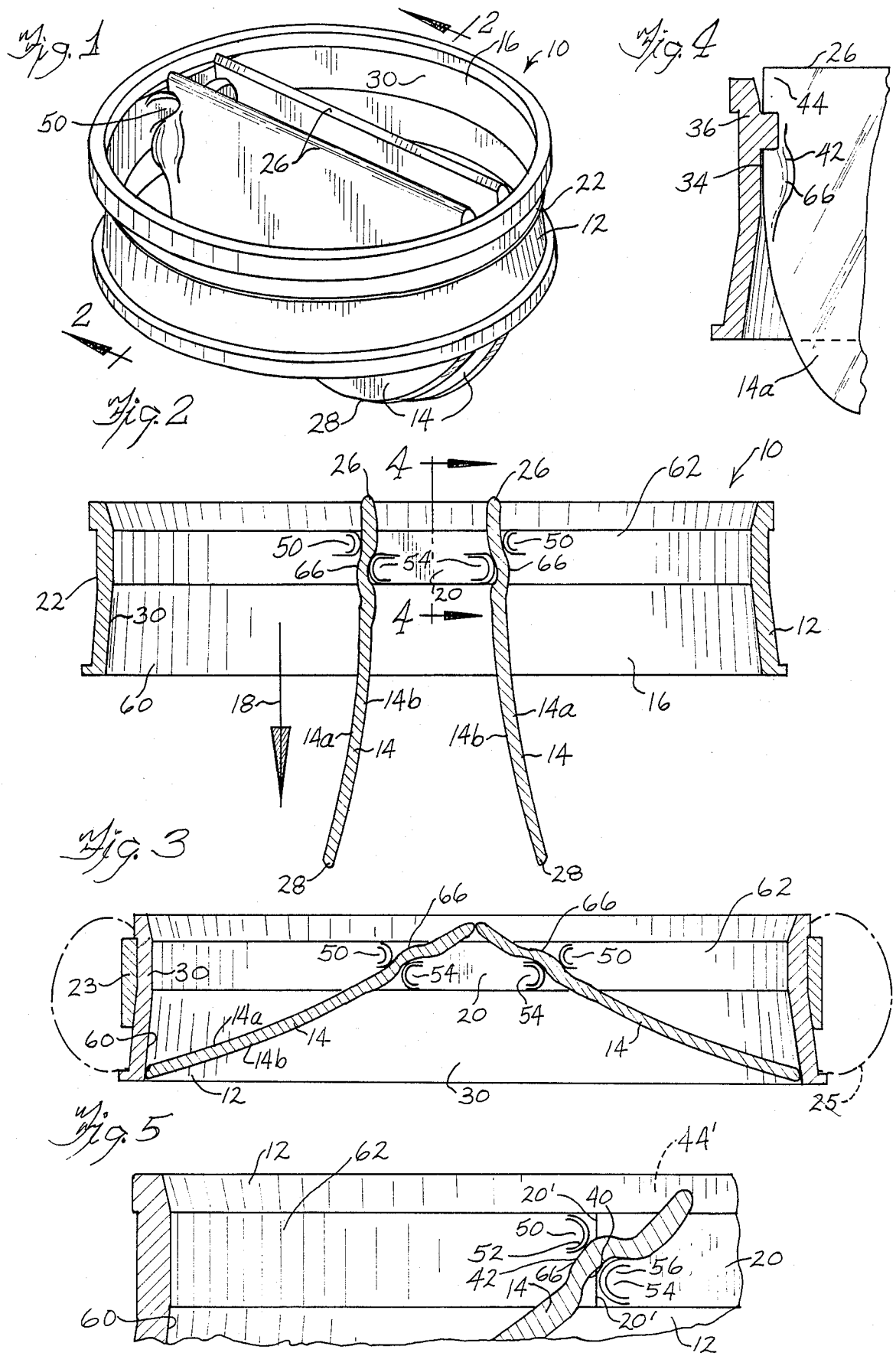

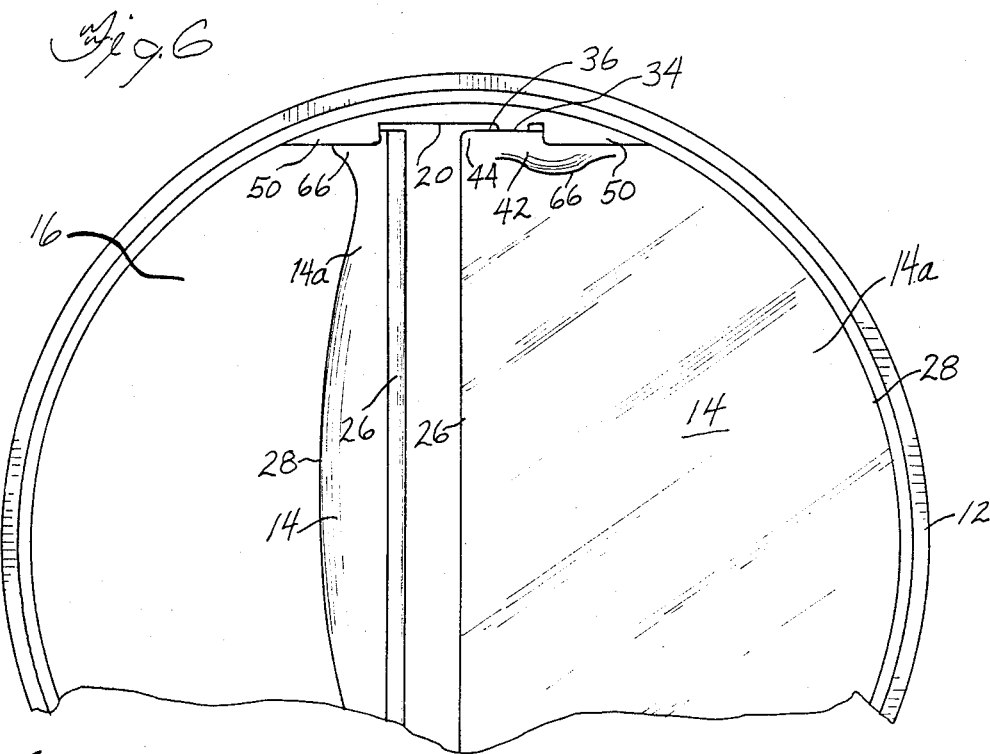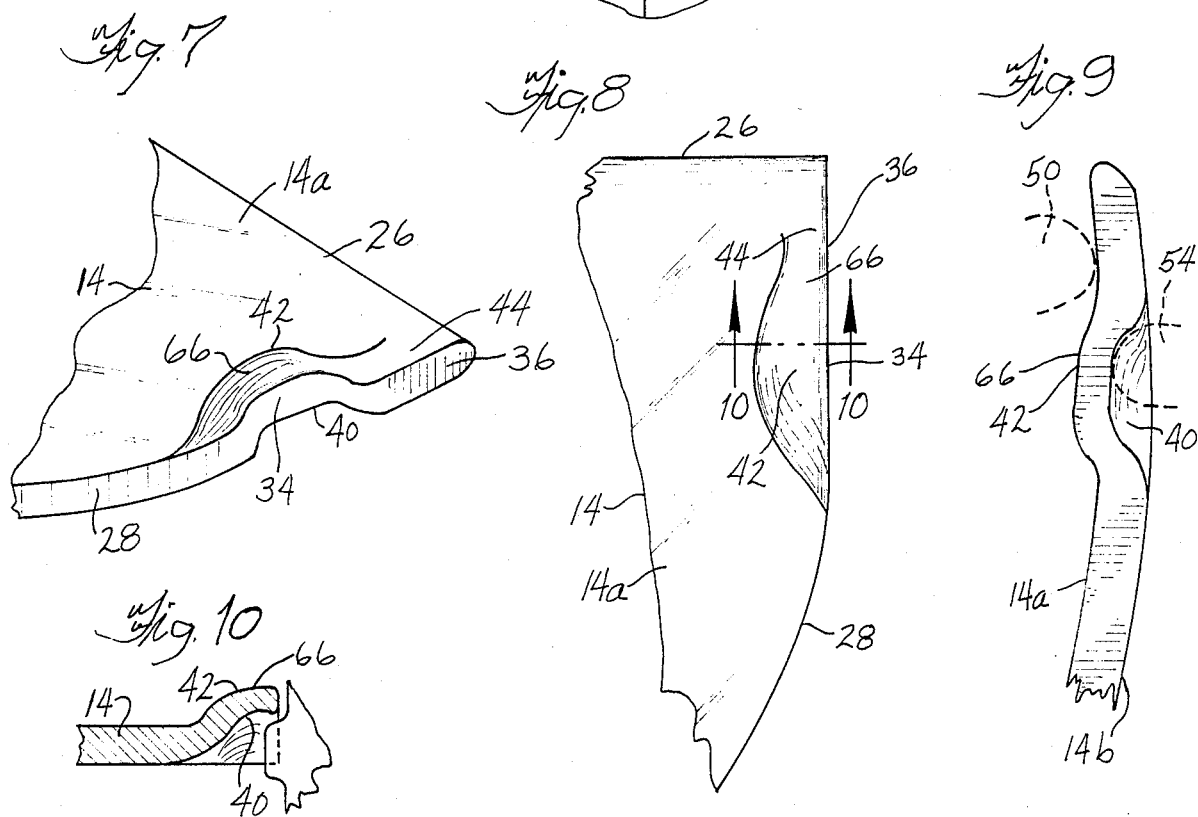

BI-LEAFLET HEART VALVE

BACKGROUND OF THE INVENTION

1. Field of the Invention

The present invention pertains to heart valve prostheses and in particular, to bi-leaflet heart valve prostheses using pivotable valve members.

2. Description of the Prior Art

Various types of heart valve prostheses have been developed which operate hemodynamically as a result of the pumping action of the heart. Among the types of heart valves which have been developed are valves having single disk occluders which pivot along an eccentric axis to open and close the heart valves, such as that described in U.S. Pat. Nos. 4,306,319 and 4,011,601, and bi-leaflet heart valves, such as those described in U.S. Pat. Nos. 3,903,548 and 4,605,408. The above-mentioned patents have various arrangements for pivotally connecting the valve or valves to a body member. However, the need continues for improved heart valves which are intended for permanent implantation into the human heart.

In its open position, a valve should provide a passageway which is large and which has good flow characteristics so that blood flows freely therethrough with a minimum of drag and eddy currents. The heart valve should be responsive to blood flow to quickly open during the pumping stroke of the heart and snap back quickly when the heart relaxes to prevent regurgitation of the blood. The heart valve must, of course, be biocompatible and thrombo-resistant, and in this regard, it is important that all surfaces be well washed by blood to prevent stagnation which might lead to eventual clotting. The opening and closing of the valve should be sufficiently soft so that the patient is not disturbed by the sounds produced. Furthermore, the action of the valve should be such that it does not cause hemolysis (breaking of blood cells). The heart valve must withstand countless openings and closings, and particular care should be exercised so that the load-bearing surfaces, such as the pivot points and stops, do not wear out during the life of the patient. The above characteristics may be desirably achieved with a simple design which not only simplifies manufacture, but also reduces the quality control problems associated with complexity.

The interengagement structures by which valve members are mounted in heart bodies frequently represent regions where blood is most likely to clot and stagnate. Some designs of heart valves, such as those disclosed in U.S. Pat. No. 4,373,216, provide improved performance in this regard. For example, the valve mounting arrangement of U.S. Pat. No. 4,373,216 requires window-like cut-out portions at the valve lateral edges to provide clearance for guide members protruding from an inner wall of the valve body. Generally, it is desirable, if at all possible, to provide valve bodies having an internal bore of maximal size, and to provide valves fitting therein having smooth continuous edges free of windows, cutouts and the like.

SUMMARY OF THE INVENTION

Accordingly, it is an object of the present invention to provide a bi-leaflet heart valve having an inner bore of maximal size and having minimal complexity so as to provide economical manufacture.

Another object of the present invention is to provide a bi-leaflet heart valve having improved flushing at critical points of connection between the valve body and valve occluders as well as at the junction between the valve body and the sewing ring.

These and other objects of the present invention, which will become apparent from studying the appended description and drawings for a heart valve prosthesis that allows blood flow therethrough in a downstream direction. The valve includes a generally annular valve body having an interior surface defining a central passageway through which blood flows. A pair of leaflet occluders are proportioned to be pivotally received within the valve body and to move between an open position and a closed position wherein they block the reverse flow of blood in an upstream direction. Each leaflet occluder is generally disk-like, having opposed lateral edges disposed between a mating edge and an arcuate edge. A pair of upstream and downstream protuberances extend from the interior surface of the valve house to pivotally mount each leaflet. Each pair of protuberances has rounded leaflet-engaging edge surfaces generally facing each other and spaced apart so as to receive one leaflet lateral edge therebetween. Each leaflet occluder has protuberance-engaqing swells along each lateral edge thereof, and includes a concave downstream surface region and an adjacent convex upstream surface region. The concave surface regions are located on the lateral edges of each leaflet at a location between a straight edge section thereof and the leaflet arcuate edge. The leaflets are installed in the annular valve body so that the leaflet concave surface regions are associated with the respective downstream protuberances and the convex surface regions lie adjacent the upstream protuberances, maintaining the leaflets captive in the valve body. In the closed position the straight edge sections of the lateral portions form a continuous straight edge when viewed in plan, when the mating edges of the leaflet occluders are mated with each other and when the arcuate edges of the occluders abut the valve body interior surface.

BRIEF DESCRIPTION OF THE DRAWINGS

In the drawings, wherein like elements are referenced alike,

FIG. 1 is a perspective view of a bi-leaflet heart valve embodying various features of the present invention shown in its open position;

FIG. 2 is a cross-sectional view, enlarged in size, of the heart valve taken along the line 2—2 of FIG. 1 and looking in the direction of the arrows;

FIG. 3 is a cross-sectional view similar to that of FIG. 2 but showing the valve in its closed position;

FIG. 4 is an enlarged, fragmentary cross-sectional view taken along the line 4—4 of FIG. 2 and looking in the direction of the arrows;

FIG. 5 is an enlarged, fragmentary view showing the left-hand valve occluder of FIG. 3 and showing an enlarged view of the mounting arrangement thereof in an intermediate position;

FIG. 6 is a top plan view of the heart valve of the preceding Figures showing the right-hand valve occluder in its closed position and the other, left-hand valve occluder, in an open position.

FIG. 7 is a fragmentary perspective view of one lateral edge of a valve occluder.

FIG. 8 is a fragmentary top plan view, enlarged in size, of that portion of the valve occluder illustrated in FIG. 7;

FIG. 9 is an enlarged fragmentary view showing the edge of the valve occluder of FIG. 8, with the short pivot posts shown in ghost; and FIG. 10 is a cross-sectional view taken generally along the lines 10—10 of FIG. 8.

DETAILED DESCRIPTION OF THE PREFERRED EMBODIMENTS

Illustrated in FIG. 1 is a heart valve prosthesis 10 having an annular valve body or housing 12 which carries a pair of pivoting valve occluders or leaflets 14, which open and close to control the normal downstream flow of blood through a central passageway or inner bore 16 of the valve body in the downward direction of arrow 18 (see FIG. 2). Referring to FIGS. 5 and 6, the generally circular shape of the passageway 16 through valve body 12 is altered slightly by a pair of diametrical opposed flat surfaces 20 and several pairs of inward protrusions or short posts hereinafter described. The flat surfaces 20 have a small size compared to the remainder of the circumference of the passageway 16, and are confined to an area immediately adjacent the hinge mechanism for suspending the leaflets 14. As shown in FIG. 5, the flat surfaces 20 have side edges 20' which are located generally between the complementary leaflet-mounting protrusions 50, 54 of each pair. As will be seen, several advantages including reduced turbulence and stress on blood flowing past the hinge mechanism, and minimal disturbance to the washing of the hinge mechanism by blood flow therepast results from the minimally-sized flat surfaces 20.

As can be seen in FIGS. 2 and 3, for example, valve body 12 has a uniform height and defines a peripheral groove 22 at its exterior surface for accommodating a suturing ring 25 (shown in phantom in FIG. 3) which may be any of the various types already well-known in the art for sewing or suturing of the heart valve 10 to the heart tissue. A conventional suturing, preferably made of carbon-coated Dacron or the like, is confined by a lip extending from the downstream edge 60 of the valve body to prevent migration of potential thrombis-causing material from the suture ring into the interior of the valve, where it might disturb the valve operation. In this regard, it should be noted that the hinge mechanism supporting the leaflets is almost completely protected by the valve body against tissue and unraveled sutures which, if present, might protrude into the lumen. As a further advantage the divergent frustoconical exit portion of the valve body significantly reduces the risk of dislodgement of the suture ring, particularly when the suture ring is strained during the valve closure phase of the heart-pumping cycle when the valve experiences maximum loading. If desired, a metal stiffening ring 23 can be fitted around the valve body and located generally around the upstream section as depicted in FIG. 3.

The leaflets 14 may be flat, but as best seen in FIGS. 2 and 3, they preferably have a slightly concave upstream surface 14a and a slightly convex downstream surface 14b. The leaflets 14 are generally half-circular, disk-like in shape, having a generally straight inner mating edge 26 and an outer slightly elliptical or generally arcuate edge 28 for contacting the inner surface 30 of valve body 12, and more particularly the enlarged frustoconical exit portion 60 as will be explained in greater detail herein with reference to FIG. 3. Disposed between mating edge 26 and arcuate edge 28 are a pair of opposing lateral edges 34 which include a straight-line edge section 36 lying immediately adjacent mating edge 26. As shown in FIG. 2, the leaflets are parallel to each other in the area of most rapid blood flow.

Each leaflet 14 includes at its lateral edge 34, a swell-like member 66 comprising a concave surface region or recess 40 on the leaflet lower or downstream surface 14b and a convex surface region 42 on the leaflet upper or upstream surface 14a. Corner regions 44 (see FIGS. 4, 7 and 8) are defined on upper surface 14a, between the convex portion 42 and mating edge 26. The straight edge sections 36 formed at the corner regions of opposed leaflets, form a continuous straight line when a closed heart valve is viewed in plan. The straight line lies immediately adjacent valve body flat surfaces 20 when the leaflets are mounted in the valve body. As will be described in greater detail below with reference to FIG. 5, the corner region 44 can alternatively be concave with a grooved area 44' formed in upper surface 14a.

Referring especially to FIG. 5, two pairs of protrusions are provided on each flat portion 20. As best seen in the enlarged view of FIG. 5, the side edge 20' of the flat portion 20 of the valve body inner surface 30 is located between the two protrusions 50, 54 of each pair. The upper or upstream protrusion 50 of each pair has a thickened rounded edge 52 for engaging the upper surface 14a of leaflet 14. The protrusion 50 is deepest or thickest at its rounded inner edge 52 and is smoothly tapered to a minimum depth or thickness at a point where it blends into the inner surface 30 of valve body 12. Similarly, the lower or downstream protrusion 54 of each pair has a rounded thickened outer edge portion 56 for engaging the lower surface 14b of leaflet 14. The rounded edges 52, 56 of protrusions 50, 54 generally oppose each other, and their centers are generally aligned along a line forming an acute angle with the plane of the centerline or axis of valve body 12. As indicated in FIGS. 2, 3 and 5, the centers of the rounded leaflet-engaging edges of the protrusions 50, 54 preferably lie along a line at an angle of approximately 45° to the plane of the centerline; however, the line could form an angle between 20° and 60°.

During opening movement, the leaflets 14 experience pressure forcing them into contact with the downstream protrusions 54. As the leaflets approach the fully opened position illustrated in FIG. 2, the upper surfaces 14b thereof come into contact with the upstream protrusions 50, and when fully open, the leaflets are held captive within the valve body as upper protrusions 50, which cooperate in forming the stop, engage concave portions 42 adjacent corner 44. During closing movement, the pressure forces the leaflets against the upstream protrusions 50 and pivoting begins which is also guided by contact with the lower protrusions 54, as depicted in FIG. 5. The leaflet portions on either side of the swell member 66 preferably have a significantly greater thickness than the thickness of the swell member itself, as can be seen in FIG. 5. The leaflet-mounting protrusions are spaced to receive the thinner, swell portion, but not the adjacent portions of the leaflet. Hence, the leaflets are free to move without jamming or seizing and are prevented from escaping their captive engagement with the valve body because the increased thickness of the leaflet in the corner regions 44 (see FIGS. 4, 7 and 8). The concave protrusion-receiving recesses 40 are generally elongated so that the leaflets 14 undergo some translational movement in the normal flow direction upon opening as they pivot guided by the protrusions 50, 54. Similarly, the leaflets also undergo translational displacement in the opposite direction along with the backflow of blood upon closing. This movement assures a wiping action between the interengaging valve occluders and valve body components which is important in preventing thrombosis.

Referring now to FIGS. 2 and 3, another important feature according to one aspect of the present invention is the generally outwardly-flared frustoconical discharge or outflow portion 60 which is slightly larger in diameter than the entrance or inflow portion 62 of the valve body and reduces resistance to normal flow, an important feature, especially over the period of operation of an implanted prosthesis. The frustoconical exit portion effects streamlining of the blood flow particularly in combination with the concave upstream leaflet surfaces because its surface is generally parallel to the fully opened leaflets; it also offers improved seating with the leaflets upon valve closure.

Another advantage of the present invention, the reduced forward resistance is accompanied by features reducing or substantially eliminating hemolysis. For example, as mentioned above, the leaflets 14 are slightly curved so as to be concave when viewed in the flow direction 18. The upstream portions of the leaflets are parallel to normal bloodflow in the open position, thereby reducing blood turbulence and shear stress. The concave upper surface portion of the leaflets is generally parallel to the enlarged, outwardly-flared frustoconical exit portion 60 of the valve body, lowering resistance to normal flow and turbulence, thereby protecting against hemolysis, which stresses the blood cells. Further, the above-described curvature of the leaflets assures quick closing upon backflow.

The concave and convex surface regions 40, 42 are, in the preferred embodiment, formed as a unitary swelled area 66, which is preferably of generally constant thickness (see FIGS. 10). The swelled portion is dimensioned to provide clearance with the protrusions 50, 54, enabling complete flushing of that area. Further, the swelled portions are configured to allow a small, controlled amount of leakage adjacent the hinged mechanism, providing further flushing to prevent stasis and thrombis formation. With particular reference to FIG. 10, taking a section through the swelled portion, it can be seen that the upper convex region 42 and the lower concave region 40 together form a swell region 66 of generally uniform thickness generally equal to the thickness of the leaflet 14. However, the thickness of the swell portion between surface regions 40, 42, or the spacing between adjacent protrusions 50, 54, can be reduced or increased, as desired. In any event, the convex and concave bearing surfaces of the leaflet edges are preferably streamlined so as to minimize turbulence and stasis within the valve, as well as eliminating crevices and other areas which would otherwise not be thoroughly washed during the entire opening and closing cycle of the valve. As seen in the cross-sectional view of FIG. 5, for example, the lower concave surface which bears against the lower protrusion 54 is considerably longer than that needed to receive the protrusion. This lengthening of the concavity not only allows translation of the leaflet occluder during opening and closing but also provides a streamlined curvature which induces thorough wetting by blood flowing across the lower leaflet surface so as to thereby induce a washing of that particular hinge area despite any interference in the local blood flow due to the adjacent protrusion. In a similar manner, the upper convex surface region 42 is also lengthened and streamlined in the flow direction so as to induce a thorough washing of that surface. It is important to note in this regard that the protrusions are rounded and streamlined relative to the flow direction, and are aligned along a line forming an angle ranging between 20 and 60 degrees with the plane of the centerline, as explained above. When combined with the interfitting leaflet edge as in the above-described configuration, an improved thorough washing of the engaging hinge parts takes place over substantially the entire opening and closing cycles. These refinements in the configuration of the interengaging hinged parts are extremely important in providing a valve prosthesis requiring little or no anticoagulants for its successful long-time operation.

As a further feature directly contributing to the improved washing of hinged parts, the flat area 20 of the valve body is of minimal size and is positioned so as to have a minimal turbulence effect on overall blood flow, thereby further assuring adequate wetting by the blood flow across the surfaces of the interengaging hinge parts during substantially their entire cycle of operation. In this regard, the flat area 20 cooperates with the straight edge sections 36 of the leaflets in providing a seal in the closed position. Further, as indicated in FIG. 8, the swell area 66 also terminates in a straight edge aligned with the straight edge section 36. The straight edges of the leaflets are at all times maintained generally parallel to the flat portions 20 of the valve body, which provide a bearing surface for the pivoting leaflets, thereby enhancing flushing of the hinge and reducing turbulence and edge effects affecting blood flow.

Referring now especially to FIG. 3, a pivotal mounting of leaflets 14 will now be explained in greater detail. As mentioned above, the appropriate mating portions of the leaflet lateral edges are received between protrusions 50, 54. The positioning of the concave and convex surface regions relative to each other and relative to the protrusions 50, 54, provides effective capture of the leaflets and resists drag forces imparted thereto by the bloodstream, particularly drag forces tending to displace the leaflets in a downstream direction. Further, the configuration of the convex and concave surface regions and of the protrusions engaged therewith defines a precise path of rotation which allows low-resistance rapid initiation of leaflet movement toward closed position upon occurrence of initial backflow. The major upper surface of the leaflets is generally concave, and in the preferred embodiment, the leaflets are of a generally constant cross-sectional thickness. Accordingly, the major lower surface of the leaflets is generally convex with the curvature of convexity very closely matching the curvature of the concavity of the upper leaflet surface The convex downstream surface aids in providing a rapid leaflet as soon as backflow occurs and acts upon the lower ends of the leaflets. Because the lower ends of the leaflets extend below the valve body 12 and because the initiation of leaflet closure is fairly rapid, regurgitation of blood into the upstream heart chamber is effectively minimized.

The frustoconical configuration at the exit of the valve body, generally denoted by the numeral 60, provides significant advantages upon valve closure For example, the outwardly-diverging frustoconical exit portion of the valve body aids in seating the downstream ends 28 of the leaflets, and aids in orienting the swell configuration, i.e., the convex and concave surface regions 40, 42 relative to the upper and lower protrusions 50, 54, respectively. Thus, the pairs of protrusions and the frustoconical exit portion cooperate in providing a precise positioning of the leaflet, which is essential not only for proper closing of the valve, but also for desired clearance between the valve lateral edge and the protrusions necessary for thorough flushing in the localized area of the interengaging hinged parts when the valve is nearly closed A further advantage provided by the frustoconical exit portion of the valve body is the camming action it provides with the downstream ends 28 of the leaflets, urging those leaflets to undergo a controlled translational movement of well-defined length. The translational movement of the leaflets, as explained above, is particularly important for wiping the hinge mechanism and for providing a cleansing blood flow past the hinge components.

As can now be seen from the above-described features of a valve prosthesis constructed according to the principles of the present invention, not only is an improved valve operation provided, but the valve operation also positions the hinge mechanism for thorough flushing by the bloodstream, thereby enabling the valve prosthesis to be used with little or no anticoagulant, a particularly advantageous benefit for many patients in light of the complications which may develop.

It will thus be seen that the objects hereinbefore set forth may readily and efficiently be attained and, since certain changes may be made in the above construction and different embodiments of the invention without departing from the scope thereof, it is intended that all matter contained in the above description or shown in the accompanying drawings shall be interpreted as illustrative and not in a limiting sense.

What is claimed is:

1. A heart valve prothesis for allowing blood flow there through in a downstream direction, said valve comprising:
   a generally annular valve body having an interior surface defining a central passageway through which blood flows, said valve body interior surface being formed with a frustoconical downstream section opening in a downstream direction;
   a pair of leaflet occluders proportioned to be pivotally received within said valve body and to move between an open position and a closed position wherein they block the reverse flow of blood in an upstream direction, said leaflet occluders each having a generally planar main body portion with opposed lateral edges disposed between a mating edge and an arcuate edge;
   a pair of protruberances extending from said interior surface to pivotally mount each lateral edge of said leaflet occluders, the protuberances of each pair of protuberances having rounded leaflet-engaging edge surfaces generally facing each other and being spaced apart so as to receive one said leaflet lateral edge therebetween, facing each other and being spaced apart so as to receive one said leaflet lateral edge therebetween;
   protuberance-engaging means along each leaflet occluder lateral edge, including a concave downstream surface region and a generally opposed convex upstream surface region cooperating with the concave surface region to form a portion of enlarged cross-sectional thickness relative to said planar main body portion, said concave surface regions of a leaflet occluder being located on the lateral edges thereof at a location between a straight edge section thereof and said leaflet arcuate edge said concave surface regions being downwardly opening and elongated for translational movement of said leaflet occluders along said protuberances as said leaflet occluders are moved between said open and said closed positions; and
   said leaflets being installed in said annular valve body so that said downstream protuberances are received in respective leaflet concave downstream surface regions and said convex surface regions lie adjacent said upstream protuberances, said protuberances being spaced apart from each other with a preselected spacing and said leaflet lateral edges which are received between said protuberances being dimensioned so that rotational excursion of said leaflet occluders is limited by said protuberances and so that said protuberances guide said leaflet occluders for both translational and rotational movement with respect thereto as said leaflet occluders are moved between said open and said closed positions, and so that said leaflet lateral edges are retained by said protuberances so as to prevent disengagement therefrom during valve opening and valve closing.

2. A heart valve according to claim 1 wherein each said leaflet lateral edge further includes a second concave surface region formed in the upstream leaflet surface and located between said convex region and said mating edge, said upstream protuberances being received in said second concave regions when said leaflet occluders are pivoted to the open position.

3. A heart valve according to claim 1 wherein said protuberances have a maximum thickness adjacent their rounded leaflet-engaging edges and are sloped to a point of minimum thickness adjacent said valve interior surface.

4. A heart valve according to claim 1 wherein said frustoconical downstream section of said valve body interior surface is generally parallel to upstream surface portions of said leaflet occluders remote from said mating edges, when said leaflet occluders are in said open position.

5. A heart valve according to claim 1 wherein said valve body interior surface immediately adjacent said protuberances defines a flat planar surface, with remaining portions of said valve body interior surface mating with said leaflet occluders being generally curved.

6. A heart valve according to claim 3 wherein the points of maximum thickness of said protuberances lie along a line forming an arcuate angle with the axis of said valve body.

* * * * *